United States Patent [19]
Estevenel et al.

[11] 4,113,816
[45] Sep. 12, 1978

[54] PROCESS FOR THE MANUFACTURE OF LAYERED TABLETS INCORPORATING CONTROLLED-RELEASE MICROCAPSULES

[75] Inventors: Yvette Fr. M. J. Estevenel; Maurice H. Thely, both of Paris; Wladimir A. Coulon, Claye-Souilly, all of France

[73] Assignee: Choay S.A., Paris, France

[21] Appl. No.: 767,885

[22] Filed: Feb. 11, 1977

Related U.S. Application Data

[60] Continuation of Ser. No. 604,029, Aug. 12, 1975, abandoned, which is a division of Ser. No. 487,042, Jul. 10, 1974, Pat. No. 3,922,338.

[30] Foreign Application Priority Data

Jul. 12, 1973 [FR] France .................. 73 25531

[51] Int. Cl.² .............................................. B29C 6/00
[52] U.S. Cl. ................................ 264/113; 264/120; 264/122
[58] Field of Search .................. 264/113, 120, 122

[56] References Cited

U.S. PATENT DOCUMENTS

| | | | |
|---|---|---|---|
| 3,096,248 | 7/1963 | Rudzki | 264/112 |
| 3,723,589 | 3/1973 | Kennedy | 264/113 |

*Primary Examiner*—Robert F. White
*Assistant Examiner*—James R. Hall
*Attorney, Agent, or Firm*—Browdy and Neimark

[57] ABSTRACT

The present invention relates to the manufacture of new tablets for administration of medicaments, which tablets contain in their mass, controlled-release microcapsules, that is to say elemental particles coated with a protective covering which contains an encapsulated product which is gradually released in a controlled, regular and time-dependent way.

These new tablets are characterized in that they are constituted by the association of a plurality of superposed layers of which the medial layer is essentially constituted by microcapsules containing an active substance, while the exterior layers constitute means of protecting the microcapsules of the medial layer, particularly against the shock of compression when compressing them to tablets. The invention thus relates to a process for manufacturing said tablets.

9 Claims, 1 Drawing Figure

CONTROLLED RELEASE

LEGEND

| | |
|---|---|
| VERTICAL AXIS | — % ACTIVE INGREDIENT RELEASED |
| HORIZONTAL AXIS | — TIME INTERVAL |
| S CURVE | — STANDARD TYPE TABLES |
| I '' | — "AVICEL" AND CORN STARCH EXCIPIENTS |
| II '' | — CORN STARCH EXCIPIENT |
| III '' | — ALGINATE EXCIPIENT |
| IV '' | — AVICEL PH 102 AND POLYETHYLENEGLYCOL EXCIPIENT |

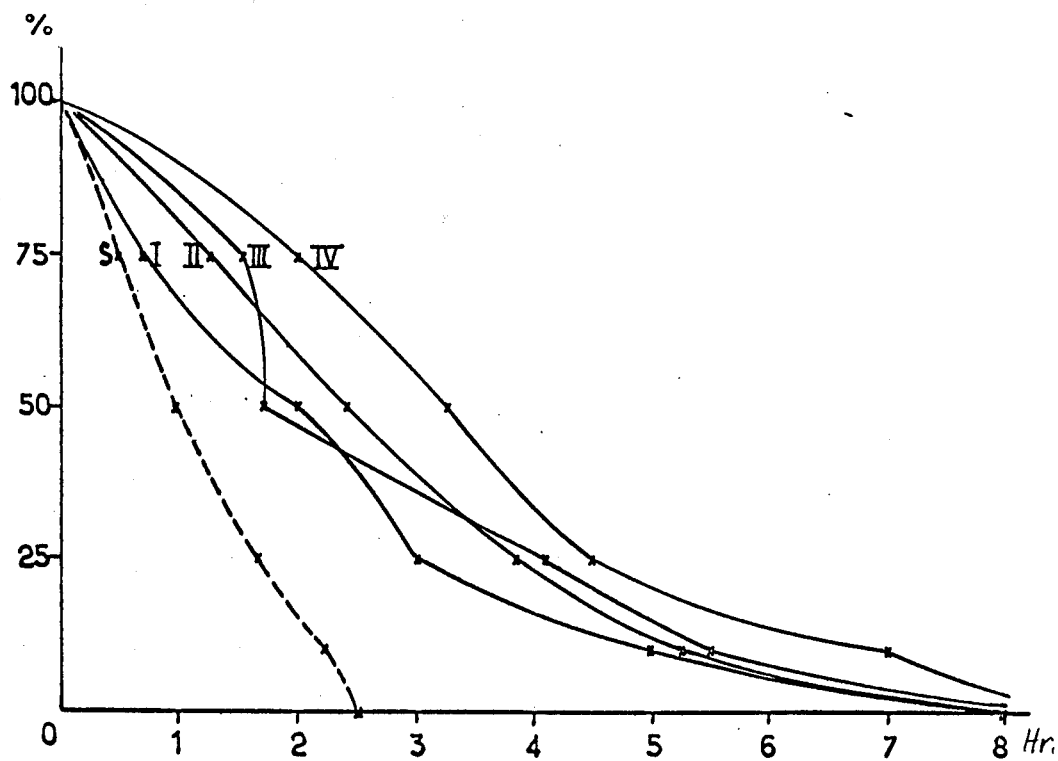
CONTROLLED RELEASE
LEGEND
VERTICAL AXIS — % ACTIVE INGREDIENT RELEASED
HORIZONTAL AXIS — TIME INTERVAL
S CURVE — STANDARD TYPE TABLES
I " — "AVICEL" AND CORN STARCH EXCIPIENTS
II " — CORN STARCH EXCIPIENT
III " — ALGINATE EXCIPIENT
IV " — AVICEL PH 102 AND POLYETHYLENEGLYCOL EXCIPIENT

PROCESS FOR THE MANUFACTURE OF LAYERED TABLETS INCORPORATING CONTROLLED-RELEASE MICROCAPSULES

This application is a continuation of Ser. No. 604,029, filed Aug. 12, 1975, now withdrawn in favor of the present application, in turn a division of Ser. No. 487,042, filed July 10, 1974 and now U.S. Pat. No. 3,922,338.

FIELD OF THE INVENTION

The present invention relates to the manufacture of new tablets containing in their mass, controlled-release microcapsules and to the method of manufacture of such tablets.

BACKGROUND OF THE INVENTION

The pharmaceutical industry has, for a long time, attempted to solve the problem of prolonging the period of effective action of medicaments. This problem is particularly important in the case where the period of effective action is short and also if there is a problem of conditioning two substances, or mixtures of substances, which are incompatible with one another in the same tablet especially when it would be advantageous to administer these substances in association with one another.

It has been proposed to solve both of these problems by producing "multi-layer" tablets in which a plurality of medicamental substances are distributed in different layers, superposed on one another by successive pressings.

The multi-layer tablets which have been produced with the object of constituting controlled-release types of medicament, comprise a plurality of superposed layers, the most common number of layers being three. Each of these layers has such a composition that the medicaments are liberated at intervals of time which are spaced apart. When the multi-layer tablets are intended to separate active constituents which are incompatible with one another, three layers are again usually provided, which comprise a thin central layer of an inert substance which separates two layers of much greater thickness, which contain the incompatible medicaments.

Nevertheless, the multi-layer tablets already known which are of the controlled-release type, that is to say, tablets which release the active ingredients in a controlled manner over a period of time, suffer from the disadvantage that is cannot be ensured that the active constituent is liberated in a programmed manner at sufficiently regular intervals.

It is for this reason that attempts have been made to find other forms which produce a controlled-release effect over a period of time. It is for this reason that microcapsules have been proposed.

The microcapsules comprise elemental particles of small dimensions, that is to say, having dimensions from a few microns to several millimeters. These microcapsules may be in a solid or liquid state and may be coated with a protective covering to form a "micro-package". This "micro-package" is capable of being destroyed by mechanical or any bio-chemical action, at the time when it is desired to use the "micro-packaged" substance. Alternatively, the structure thereof may be such that it constitutes a coating through which the active constituent is progressively liberated.

The protective coating covering the elemental particles is obtained either by chemical or mechanical methods of encapsulation. The coatings of microcapsules, which are intended to act in a controlled-release manner over a period of time, are prepared by methods known per se. In particular, it is possible to regulate the rate of external diffusion of the encapsulated product by different methods. It is particularly possible to vary the thickness, to a greater or lesser extent, of the coating and, above all, by providing the coating with a predetermined micro-porosity.

Nevertheless, these microcapsules are relatively fragile structures. Until now, it has proved impossible to put them into the form of tablets. A tablet is, of course, a very convenient form of administration since it reduces the volume to be swallowed by a patient. In fact, in the course of the process of mixing with pressing with adjuvants or other associated substances, an abrasive effect is noticed. This affects the external layer of the microcapsules and leads to at least a partial destruction of the microcapsule. This, accordingly, affects the quality of the controlled-release effect desired. Moreover, the direct pressing of the microcapsule, irrespective of whether or not the microcapsule is of the double core coating type, has the effect of destroying its external and internal structure and the tablet obtained loses all its effectiveness.

This impossibility of pressing microcapsules under satisfactory conditions whilst preserving the wholeness of the microcapsules, has necessitated the microcapsules to be hitherto used in the form of gelules. This pharmaceutical form whilst it enables the microcapsules to retain their effectiveness, nevertheless suffers from a disadvantage which is of some consequence, that is to say, it is difficult to swallow. Moreover, this format is unsuitable when one attempts to associate microcapsules with one or more other active substances. In fact, not only does this entail extremely large gelules, but additionally, the operation of mixing the microcapsules with other granulated active agents has an abrasive effect due to the contact of the microcapsules with one another. The resultant erosion of the microcapsules has the effect of annoyingly affecting the controlled-release.

SUMMARY OF THE INVENTION

The object of the present invention is to provide a process for manufacturing new tablets which contain controlled-release microcapsules in their mass, which respond better to the necessities of the art than controlled-release agents previously known. In particular, it is an object of the process of the invention to provide new tablets which permit the use of microcapsules which allow the controlled-release of the active constituent in a regular and time-dependent manner, while at the same time permitting an important reduction in the dimensions of the pharmaceutical preparations including microcapsules.

According to the present invention, there are produced new tablets containing, in their mass, controlled-release microcapsules, characterised in that they are constituted by the association of a plurality of superposed layers, of which the medial layer is essentially constituted by microcapsules containing an active substance, whilst the exterior layers - which may possibly also contain identical or different active substances and which have a composition usual for the making of tablets - constitute means of protecting the microcapsules of the medial layer, particularly against the shock of compression.

According to an advantageous embodiment of the invention, the tablets in accordance with the invention have a hardness of the order of 10 to 20 kg on their surface and of the order of 8 to 16 kg on their periphery.

According to a preferable embodiment of the invention, the ratio between the sum of the thicknesses of the external layers and the thickness of the medial layer containing the microcapsules, is advantageously between 0.8 and 4 and preferably between 1 and 2.4.

According to the present invention there is provided a method of making tablets containing, within their mass, controlled-release microcapsules characterised in that they are prepared in a tablet-making machine, a first external layer - which essentially comprises excipients, and possibly therapeutically active substances - which is subjected to a light compression, by simple levelling, for example, in that an internal layer superposed on the first external layer is prepared, the internal layer essentially comprising microcapsules containing an active substance, which internal layer is subjected to a light compression, by simple levelling, for example, in that a second external layer is prepared, of which the composition is identical to, or different from, that of the first external layer, which is superposed on the internal layer of microcapsules, after which the superposed layers are subjected to compression in a machine for making tablets, which exerts a pressure force capable of giving rise to tablets of which the cohesion is sufficient to ensure the disintegration of the tablet in accordance with the conditions required by the French Pharmacopoeia.

According to an advantageous embodiment of the process according to the present invention,, the microcapsules containing an active substance, are associated, in the medial layer, with an excipient which favors the disintegration of the microcapsules. By putting the process in accordance with the present invention into effect, there are obtained tablets in which the microcapsules contained in the medial layer are not damaged during the compression process due to the presence of external layers of a sufficient thickness which protects the medial layer on each side.

Test carried out by the applicant have shown that for a medial layer thickness of between 0.6 and 3 millimeters, and preferably between 1 and 2 millimeters, the thickness of each of the external layers must be between 0.8 and 2 millimeters and preferably between 1 and 1.2 millimeters. The tablets obtained in accordance with the present invention have associated therewith the advantage inherent in their presentation in the form of tablets, that is to say, the administration of active substances in a small volume together with the advantage of microcapsules, that is to say, a controlled-release of one or more active substances in a programmed manner with respect to time.

DESCRIPTION OF PREFERRED EMBODIMENTS

The carrying out of the process in accordance with the present invention will now be described in greater detail.

A composition adapted to form the external layers of the final tablet is prepared. This composition essentially comprises excipients to which may possibly be added active substances; the excipients advantageously comprise an excipient of appropriate charge, for example, a microcrystalline γ-cellulose such as that which is known under the trade name of "AVICEL PH 102" (sold particularly by the firm "SEPIC"), associated with a corn starch and with a lubricant such as for example, a mixture of mono- di- and tri-palmitostearic esters of glycerol such as those which are sold (by Etablissements GATTEFOSSE) under the trade name of "PRECIROL". Into such a composition can be introduced active substances which are incompatible with those contained in the microcapsules, or active substances which are immediate-acting compared with the active substances contained in the microcapsules which act progressively over a period of time. Alternatively, the composition may contain active substances which act at a level of gastro-intestinal transit different from that of the substance contained in the microcapsules.

This composition is put into the form of granules which have a grain size identical to that of the microcapsules, so that the free flow in the tablet machine can be identical in the two compositions.

A composition adapted to form the medial layer of the final tablet is then prepared by association of the microcapsules containing the active substance, with an excipient which improves the free flow and which facilitates the disintegration and, in so doing,. the splitting of the tablets. Half of the quantity of the external layer composition is introduced into the matrix of a tablet-making machine, in which it is subjected to a light compression with a punch which is just sufficient to level this first external layer. After levelling of the first external layer, the medial layer composition prepared is superposed thereon. This is then subjected to a light compression with a punch, which is, again, just sufficient to level it. A second external layer constituted by the other half of the external layer composition is then superposed on the medial layer containing the microcapsules. The assembly of the three superposed layers is then subjected, in a tablet-making machine, to a compressive force which is a function, in particular, of the nature of the products being made into tablets, and which produces tablets having a hardness, when measured on a Stokes apparatus, lying within the range of 10 to 20 kg on its surface and of 8 to 16 kg around its periphery. Such a hardness value is sufficient, in the pharmaceutical condition art, to ensure the wholeness of the microcapsules is preserved.

The tablets thus obtained are advantageously flat and bevelled having a diameter of the order of 11 mm, a final weight of between 0.360 and 0.660 grams, and a final total thickness of between 3.3 and 5.65 mm, the thickness of each of the external layers being between 0.8 and 2 mm if the thickness of the medial layer is of the order of 0.6 to 3 mm and preferably between 1 and 2 mm. Besides the embodiments described herein before, the invention also comprises other embodiments, which will be apparent from the following description.

The invention will be further described, purely by way of example, with reference to the following non-limitative Examples which show methods of preparing new tablets in accordance with the invention.

EXAMPLE 1

1. A composition adapted to form the external layers of the final tablet is prepared by mixing the following constituents in the proportions stated:

Active constituents :

-continued

| | | |
|---|---|---|
| Hesperidine methyl-chalcone | 0.065 | g |
| Aspirin | 0.100 | g |
| 4-chloro-1-dehydro-methyl-testosterone | 0.00165 | g |
| Excipients | | |
| Lubricants such as, for example, a mixture of mono-, di- and tri-palmitostearic esters of glycerol (known in particular, under the trade name of "PRECIROL") | 0.00175 | g |
| Corn Starch | 0.050 | g |
| Filler excipient such as for example, microcrystalline α-cellulose (known under the trade name of "AVICEL PH 102") Q.s.p. | 0.260 | g |

This mixture is put into the form of granules of a grain size identical to that of the microcapsules, in such a manner that the dispersion in the tablet making machine of this composition is identical to that of the microcapsules. In practice, the granules obtained have a grain size less than 1000 μ.

2. A composition adapted to form the medial layer of the final tablet is prepared, by mixing the following constituents in the proportions stated:

| | | |
|---|---|---|
| Active constituent : | | |
| Microcapsules enclosing papaverine chlorhydrate of the order of | 0.097 | g |
| Filler excipient favoring free flow, such as "AVICEL PH 102" for example Q.s.p. | 0.140 | g |

3. (a) 0.130 g of the composition described in (1) is placed into the matrix of a tablet machine, and is subjected to a pressing, by levelling for example, with the aid of the suitable means such as the punch of the machine, without, however, supplying a compressive force to this latter. (b) On the external layer thus produced, the composition described in (2) is superposed and this is also subjected to a pressing, by levelling for example, with the aid of suitable means such as the punch of the machine, in such a manner that the punch only exerts the compressive force exercised by its own weight. (c) On the microcapsule layer is then superposed 0.130 g of the composition described in (1). (d) The multi-layer composition thus obtained, comprising a medial layer of microcapsules protected by two external layers, is submitted to a suitable compressive force in a tablet machine in such a manner as to obtain tablets having a hardness sufficient to be pharmaceutically satisfactory while nevertheless, permitting a disintegration conforming to the standards laid down in the French Pharmacopoeia and preserving the programmed controlled-release of the active constituents.

The tablet obtained by using the method which has just been described is a flat tablet, chamfered, having a diameter of 11 mm, a final thickness of 3.8 mm and a final weight of 0.400 g. This disintegrates in a period of 35 minutes. The thickness of each of the external layers is 1.07 mm whilst the thickness of the microcapsule layer is 1.65 mm.

The hardness of this tablet measured on Stokes apparatus is 10 kg on its surface and 5 kg on its periphery.

The process of the tablets in accordance with the present invention which have just been described cause the immediate liberation of the therapeutic agents contained in their external layers and the controlled-release, over a prolonged period of time, up to 8 hours, of the papaverine contained in the microcapsules of the medial layer. One practical application shows a particular interest in the case of medicaments of which the therapeutic action is transient, such as is the case with papaverine, because it allows a progessive controlled-release of the papaverine in the patient, and thus maintains a constant amount of medicament. The application of the new pharmaceutical form in accordance with the present invention, to the administration of other medicaments of which the therapeutic action is fleeting, such as adrenaline, and trinitrine, is of major interest.

The present invention also shows a great interest in the case where it is desired to administer one substance which it is desired to maintain at a regular level in the patient for a long period of time, without having to greatly increase the number of doses or by giving extremely large doses; this being the case, for example, with hypnotic or tranquilizing substances.

The form of administration is also particularly interesting in that it allows the association of microcapsules with other therapeutic substances, notably in that it allows association of two or more substances of which the actions are complementary or potentialise one another, such as is the case with the association of a delaying product and a non-delaying product, or with the association of a hypnotic agent having immediate action with a hypnotic agent having a delayed action.

EXAMPLE 2

Other excipients besides "AVICEL PH 102" described in Example 1 have been tested in association with the microcapsules of the medial layer containing the active constituent, such as papaverine chlorhydrate as described in Example 1. The efficiency of these excipients has been studied. The efficiency criterion chosen in the tests which will be described hereinafter, is the time of release in vitro of micro-encapsulated papaverine chlorhydrate. This is a function of the excipient associated with the microcapsules. This test has made it clear, in the first place of the role of the excipient, which plays a complementary role in the protection of the microcapsules, preventing these latter from sticking together and from being damaged during the preparation of the tablets, which have the result of affecting the controlled-release effect.

The process also makes clear, in the second place, the importance of the choice of the excipient, which must not have too great an adhesiveness, which raises the risk of conferring a too strong cohesion on the microcapsules before compression, thus preventing them from satisfactorily disintegrating. The choice of the excipient must, on the contrary, favor the disintegration of the microcapsules. The studies which will be described hereinafter compare the release times in vitro of micro-encapsulated papaverine chlorhydrate associated with different excipients as follows:

1. "AVICEL" plus corn starch
2. Maize starch
3. Alginate
4. Polyoxyethyleneglycol (POEG) + "AVICEL"

The test on the liberation of papaverine chlorhydrate consists in placing the sample in a disintegration apparatus of the type described in the American Pharmacopoeia, Edition XVIII, and to simulate the progressive passage from the gastric medium to the intestinal medium at 37° C ± 1° C.

The compositions of the gastric and intestinal medias are those described on pages 1026 and 1027 respectively of the American Pharmacopoeia. The pH of the gastric medium is adjusted to 1.6 and the pH of the intestinal medium is adjusted to 5.0. However, this latter does not contain any pancreatin, which is inactive at this pH. The sample is immersed for an hour in a bath containing only the gastric medium at 37° C. Every hour thereafter, half the volume of the bath is removed and replaced by an equal volume of intestinal medium.

The results obtained with these different excipients are, in other respects, compared with the time of liberation of the micro-encapsulated papaverine chlorhydrate associated with "AVICEL" in the standard tablets (that is to say, made according to conventional pharmacotechnical methods for the obtaining of classical non-multilayer tablets; in the description which follows, the expression "standard tablets", is always used in this manner). The results of this study are shown in Table I below, as well as in the accompanying drawing.

TABLE I

Time of liberation in vitro of micro-encapsulated papaverine chlorhydrate. Comparison with standard tablets and with microcapsules alone. - Incidence of the nature of the excipients.

| % of papaverine | Micro-capsules alone | Standard tablet "AVICEL" Curve S | Multilayered tablets in accordance with the invention | | | |
|---|---|---|---|---|---|---|
| | | | "AVICEL" + starch Curve I | Maize Starch Curve II | Alginate Curve III | POEG +AVICEL Curve IV |
| 25 | 2 h25 | 0 h30 | 0h40 | 1 h15 | 1 h35 | 2 h00 |
| 50 | 6 h00 | 1 h00 | 2h00 | 2 h25 | 1 h45 | 3 h15 |
| 75 | >10 h | 1 h40 | 3h00 | 3 h50 | 4 h05 | 4 h30 |
| 90 | " | 2 h15 | 5h00 | 5 h15 | 5 h30 | 7 h00 |
| 100 | " | 2 h30 | 8h00 | 8 h00 | >8 h | >8 h |

The accompanying drawing shows the curves obtained corresponding to Table I, to wit: The curve S corresponds to standard type tablets, that is to say, to tablets comprising microcapsules containing papaverine chlorhydrate, made, as indicated above, according to usual pharmacotechnical methods for obtaining of non-multi-layer classical tablets.

Curves I to IV relate to multi-layer tablets in accordance with the invention, in which:

Curve I: the active constituent of the medial layer is associated with "AVICEL" and corn starch;

CURVE II: the active constituent of the medial layer is associated with maize starch;

Curve III: the active constituent of the medial layer is associated with alginates;

Curve IV: the active constituent of the medial layer is associated with "AVICEL PH 102" and polyoxyethyleneglycol.

Table I above, as well as the curves shown in the accompanying drawing show very clearly the extended and progressive controlled-release with respect to time of tablets containing microcapsules; moreover, the superiority of certain excipients (notably AVICEL PH 102 + polyoxyethyleneglycol) is also clearly shown.

EXAMPLE 3

The compositions described in Example 1 are prepared, and by putting into operation the process described in that Example, tablets of different weights having various thicknesses of layers are prepared, in particular:

Tablets B.

| Diameter | 11 | mm |
|---|---|---|
| Weight | 0.660 | grams |
| Total thickness | 6.20 | mm |
| Medial layer (microcapsules) | 1.67 | mm |

-continued

Tablets B.

| External layers (each) | 2.25 | mm |
|---|---|---|

Tablets C.

| Diameter | 11 | mm |
|---|---|---|
| Weight | 0.270 | grams |
| Total thickness | 2.90 | mm |
| Medial layer (microcapsules) | 1.68 | mm |
| External layers (each) | 0.61 | mm |

The time of liberation in vitro of micro-encapsulated papaverine chlorhydrate is then studied as a function of the respective thicknesses of the two external layers and the medial layer. Table II below shows clearly the liberation times : — in the case of tablets such as those described in Example 1 (column 6), — in the case of tablets B above (column 7), — in the case of tablets C above (column 5) and comparing them with the time of liberation of the papaverine chlorhydrate, obtained : — in the one case with microcapsules alone, containing papaverine chlorhydrate (column 2), — in the second case with tablets of standard type, that is to say tablets constituted by microcapsules containing papaverine chlorhydrate, manufactured in accordance with usual methods for the obtaining of classical tablets of non-multi-layer type (column 3), — and in the third case with an association of constituents mentioned in Example 1, in the form of a simple mixture and not in the form of multilayer tablets in accordance with the present invention (column 4).

TABLE II

Time of liberation in vitro of micro-encapsulated papaverine chlorhydrate- Incidence of the thickness of the layers.

| % of papaverine chlor-hydrate liberated | Micro-cap-sules only | Stan-dard tablets | Mix-ture not tablet-ted | Multilayer tablets in accordance with the invention | | |
|---|---|---|---|---|---|---|
| | | | | external layer 0.6 mm | external layer 1.07 mm | external layer 2.25mm |
| (1) | (2) | (3) | (4) | (5) | (6) | (7) |
| 25 | 2 h25 | 0 h30 | 1 h00 | 0 h35 | 0 h40 | 0 h50 |
| 50 | 6 h00 | 1 h00 | 2 h20 | 1 h15 | 2 h00 | 2 h00 |
| 75 | >10h | 1 h40 | 5 h00 | 2 h15 | 3 h00 | 3 h00 |
| 90 | " | 2 h15 | 8 h00 | 3 h30 | 5 h00 | 5 h00 |
| 100 | " | 2 h30 | 10 h00 | 4 h00 | 8 h00 | 8 h00 |

1. Column relating to microcapsules alone:

This relates to the study of the liberation time in vitro of papaverine chlorhydrate for the microcapsules per se. It is to be noted that after 10 hours, the liberation of the papaverine is extremely slow.

2. Column relating to standard tablets:

This relates to tablets having been subjected to a classical compression. In this case, during the course of the compression, the microcapsules of the superficial layer have suffered a deterioration which gives them a type of "paraffin" appearance, which prevents the damping necessary for disintegration.

To permit the testing of the liberation of the papaverine chlorhydrate, the tablets had to be broken by hand to allow the disintegration and the dosage in vitro: the results obtained indicate that there is no improvement in the controlled-release and that the encapsulated microgranules have been damaged by tne compression.

3. Column relating to the non-tabletted association:

This study shows the incidence of excipients and of the other possibly associated substances on the time of release of the papaverine.

It can be stated that the other substances which are put into the preferred composition diminish the liberation time of the papaverine (compare columns 2 and 4). It is also necessary to compare the results obtained with multi-layer tablets in accordance with the invention to those obtained by the association of microcapsules and other excipients (compare columns 5, 6 and 7 with column 4). The study of the above details leads to the conclusion that the thickness of the external layers must not be less than 0.8 mm; it must be between 0.8 and 2 mm, and preferably between 1 and 1.2 mm.

For the pressure forces such as those utilized, that is to say, leading to a disintegration of the tablet in accordance with the conditions laid down in the French Pharmacopoeia, the superficial part of the medial layer, that is to say about 0.2 mm on either side of this middle layer, are found to be damaged at the moment of compression, for external layers which, as stated hereinbefore, are of a thickness of 0.8 to 1.07 mm. The medial layer can therefore have a thickness advantageously lying between 0.6 and 3 mm, and preferably between 1 and 2 mm.

EXAMPLE 4

The principle characteristics of the compressed tablets according to this invention have been verified and more particularly:
- their hardness
- their speed of disintegration
- the times required for liberating the active principal of the compressed tablet, on tablets made on industrial machines of the Layer-Press type made by Manesty the composition of these tablets being as follows:

| | | |
|---|---|---|
| exterior layers | - Starx 1500 corn starch | 0.06g |
| | colorant: Coccine | 0.0005 |
| | "Avicel PH102" Q.S.P. | 0.600g |
| medial layer | - Microcapsules of | |

| | | |
|---|---|---|
| | papaverine chlorhydrate | 0.112 |
| | polyoxyethyleneglycol 4000 | 0.06g |
| | "Avicel PH102"/starch (granules) Q.S.P. | 0.400g |
| while varying: | - the speed of rotation of the machine from 600 tablets/min. to 1400 tablets per minute, - the pressure of compression, that is the pressure which counterbalances the pressure exerted on the upper punches from 2.8 tons to 4 tons. | |

The tests have been carried out using four portions — or sub lots — numbered from I to IV, of the same fabrication lot, Lot 74056 PP, each of these parts corresponding to one of the parameters that were varied, and which have been mentioned above.

The results obtained are tabulated in Table III, which follows, from which it is evident that the tablets conforming to the present invention present a great hardness and a great cohesion, while disintegrating rapidly.

TABLE III

MULTILAYERED TABLETS CONTAINING CONTROLLED-RELEASE MICROCAPSULES ACCORDING TO THE INVENTION

| Fractions | Weight per Unit | Thickness in MM | Speed Rpm | Compensatory pressure | Hardness on edges | Hardness on faces | Disintegration | 25% of P.A. liberated in: | 50% of P.A. liberated in: | 75% of liberated in: |
|---|---|---|---|---|---|---|---|---|---|---|
| I | 1,05 g | 5,8 | 600 | 3 t | ≧13 k | 14,5 k | 30" | 2 H 45 | 5 H | 7 H 15 |
| II | 1,12 g | 5,8 | 800 | 4 t | ≧15 k | 19 k | 1'7" | 2 H 30 | 4 H 30 | ≧8 H |
| III | 1,09 g | 5,7 | 1000 | 4 t | ≧16 k | 19,5 k | 46" | 2 H 30 | 3 H 45 | 5 H |
| IV | 1,09 | 5,6 | 1400 | 2,8 t | ≧14 k | 17 k | 1' | 2 H | 5 H 45 | >8 H |

Compression accomplished on a "Manesty" type Layer-press Punches 16 mm chamfered plates
P.A. = Microencapsulated papaverine chlorohydrate It will be seen from the preceding description that the process of the present invention allows the obtaining of new tablets containing, in their mass, controlled-release microcapsules, which show important advantages with respect to the prior art, and in particular, that of permitting administration in a small volume, of one or more active substances, of which the liberation in the patient is programmed.

Various minor modifications can be made to the present invention without departing from scope thereof. Thus, it will be readily appreciated that the preceding Examples refer to the controlled-release, with respect to time, of papaverine. It will be readily apparent that the present invention gives the optimum results and it will be understood that other micro-encapsulated medicaments can be put into a form which conform to the present invention and which will give equally satisfactory results. Moreover, utilization of multi-layer compounds containing microcapsules in their mass can extend to fields other than therapeutics (for example, the progressive liberation of insecticides, disinfectants and coloring materials).

What we claim is:

1. A process of making layered tablets having upper and lower surfaces and a peripheral surface and incorporating controlled-release microcapsules, comprising:
   (a) depositing in a tablet-making machine a bottom external layer comprising essentially excipients in granular form and levelling the upper surface of said layer by a tamping action;
   (b) depositing on said levelled layer a superposed layer comprising microcapsules containing a pharmaceutically active substance, and similarly levelling said microcapsule layer;
(c) depositing on said levelled microcapsule layer a superposed top external layer comprising excipients in granular form; and
(d) then compressing said superposed layers by a force sufficient to bond the granules and microcapsules without crushing the latter to produce tablets having a hardness of about 10 to 20 kg on the said upper and lower surfaces and about 8 to 15 kg on the peripheral surface.

2. A process according to claim 1, wherein the external layers also contain active substances.

3. A process according to claim 1, wherein the external layers are identical compositions.

4. A process according to claim 1, wherein the external layers are of different composition from each other.

5. A process according to claim 1, wherein the ratio between the sum of the thicknesses of the external layers and the thickness of the internal layer containing the microcapsules is between 0.8 and 4.

6. A process according to claim 1, wherein the ratio between the sum of the thicknesses of the external layers and the thickness of the internal layer containing the microcapsules is between 1 and 2.4.

7. A process according to claim 1, wherein said microcapsules containing a pharmaceutically active substance are associated in the internal layer with an excipient which causes the disintegration of the microcapsules on subsequent administration.

8. A process according to claim 1 wherein said excipients are chosen from a group consisting of microcrystalline cellulose, starch, alginate and polyoxyethyleneglycol and said external layers are in the form of granules having the same grain size as said microcapsules.

9. A process according to claim 1 in which the granular excipients are selected from the group consisting of lubricants, fillers and mixtures thereof, and the respective thicknesses of the external layers and the internal layer being such that the ratio between the sum of the thicknesses of the external layers and the thickness of the internal layer containing the microcapsules is between 0.8 and 4.0.

* * * * *